United States Patent
Clark

(10) Patent No.: US 10,220,184 B2
(45) Date of Patent: *Mar. 5, 2019

(54) MULTI-LUMEN CATHETER

(71) Applicant: Aegis Medical Technologies, LLC, Philadelphia, PA (US)

(72) Inventor: Timothy W. I. Clark, Philadelphia, PA (US)

(73) Assignee: AEGIS MEDICAL TECHNOLOGIES, LLC, Philadelphia, PA (US)

( * ) Notice: Subject to any disclaimer, the term of this patent is extended or adjusted under 35 U.S.C. 154(b) by 297 days.

This patent is subject to a terminal disclaimer.

(21) Appl. No.: 15/149,812

(22) Filed: May 9, 2016

(65) Prior Publication Data

US 2016/0250441 A1 Sep. 1, 2016

Related U.S. Application Data

(63) Continuation of application No. 13/453,663, filed on Apr. 23, 2012, now Pat. No. 9,333,321, which is a
(Continued)

(51) Int. Cl.
*A61M 25/14* (2006.01)
*A61M 25/00* (2006.01)
(Continued)

(52) U.S. Cl.
CPC ........ *A61M 25/003* (2013.01); *A61M 1/3496* (2013.01); *A61M 1/3661* (2014.02);
(Continued)

(58) Field of Classification Search
CPC ........ A61M 25/003; A61M 2025/0031; A61M 2025/0037; A61M 1/3661
See application file for complete search history.

(56) References Cited

U.S. PATENT DOCUMENTS 256,590 A 4/1882 Pfarre
272,651 A 2/1883 Coates
(Continued)

FOREIGN PATENT DOCUMENTS

CA 1092927 1/1981
CA 1150122 7/1983
(Continued)

OTHER PUBLICATIONS

Supplementary European Search Report dated Mar. 4, 2016, for corresponding European Patent Application No. EP13781070.
(Continued)

*Primary Examiner* — Laura A Bouchelle
(74) *Attorney, Agent, or Firm* — Gordon Rees Scully Mansukhani, LLP

(57) ABSTRACT

The invention provides a catheter for placement within a vessel of a patient. The catheter comprises an elongated catheter body, a septum extending longitudinally through the interior of the catheter body from the dividing the interior of the catheter body into a first lumen and a second lumen. Each lumen has curved or angled internal walls at the distal end of the catheter that terminate at ports located on opposing sides of the catheter body. The invention also provides a method for exchanging fluids in a patient comprising the step of positioning the catheter of the present invention in communication with a fluid-containing vessel of a patient. The method is particularly well-suited for hemodialysis, plasmapheresis, and other therapies which require removal and return of blood.

16 Claims, 13 Drawing Sheets

Related U.S. Application Data continuation-in-part of application No. 12/479,257, filed on Jun. 5, 2009, now Pat. No. 8,517,978, which is a continuation of application No. 11/103,778, filed on Apr. 12, 2005, now Pat. No. 7,569,029.

(60) Provisional application No. 61/477,815, filed on Apr. 21, 2011, provisional application No. 60/561,430, filed on Apr. 12, 2004.

(51) Int. Cl.
*A61M 1/36* (2006.01)
*A61M 1/34* (2006.01)

(52) U.S. Cl.
CPC ... *A61M 25/007* (2013.01); *A61M 2025/0031* (2013.01); *A61M 2025/0034* (2013.01); *A61M 2025/0037* (2013.01)

(56) References Cited

U.S. PATENT DOCUMENTS

| | | | |
|---|---|---|---|
| 701,075 A | 5/1902 | McCully | |
| 2,175,726 A | 10/1939 | Gebauer | |
| 2,819,718 A | 1/1958 | Goldman | |
| 3,634,924 A | 1/1972 | Blake et al. | |
| 4,072,146 A | 2/1978 | Howes | |
| 4,098,275 A | 7/1978 | Consalvo | |
| 4,134,402 A | 1/1979 | Mahurkar | |
| 4,180,068 A | 12/1979 | Jacobsen et al. | |
| 4,403,983 A | 9/1983 | Edelman et al. | |
| 4,406,656 A | 9/1983 | Hattler et al. | |
| 4,451,252 A | 5/1984 | Martin | |
| 4,543,087 A | 9/1985 | Sommercom et al. | |
| 4,568,329 A | 2/1986 | Mahurkar | |
| 4,583,968 A | 4/1986 | Mahurkar | |
| 4,619,643 A | 10/1986 | Bai | |
| 4,692,141 A | 9/1987 | Mahurkar | |
| 5,221,255 A | 6/1993 | Mahurkar et al. | |
| 5,348,536 A | 9/1994 | Young et al. | |
| 5,378,230 A | 1/1995 | Mahurkar | |
| 5,380,276 A | 1/1995 | Miller et al. | |
| 5,395,316 A | 3/1995 | Martin | |
| 5,403,291 A | 4/1995 | Abrahamson | |
| 5,405,341 A | 4/1995 | Martin | |
| 5,464,398 A | 11/1995 | Haindl | |
| 5,571,093 A | 11/1996 | Cruz et al. | |
| 6,001,079 A | 12/1999 | Pourchez | |
| 6,190,349 B1 * | 2/2001 | Ash | A61M 25/0021 138/115 |
| 6,409,700 B1 | 6/2002 | Siegel, Jr. et al. | |
| 6,461,321 B1 | 10/2002 | Quinn | |
| 6,620,139 B1 | 9/2003 | Plicchi et al. | |
| 6,719,749 B1 | 4/2004 | Schweikert et al. | |
| 6,758,836 B2 | 7/2004 | Zawacki | |
| 6,786,884 B1 | 9/2004 | DeCant, Jr. et al. | |
| 7,141,035 B2 * | 11/2006 | Haggstrom | A61M 25/0068 604/43 |
| 7,569,029 B2 * | 8/2009 | Clark | A61M 25/0023 604/266 |
| 8,517,978 B2 * | 8/2013 | Clark | A61M 25/0023 604/4.01 |
| 8,696,614 B2 | 4/2014 | Gregersen et al. | |
| 2003/0144623 A1 * | 7/2003 | Heath | A61M 25/0023 604/4.01 |
| 2004/0167463 A1 | 8/2004 | Zawacki et al. | |
| 2005/0228339 A1 | 10/2005 | Clark | |
| 2005/0277862 A1 | 12/2005 | Anand | |
| 2009/0192435 A1 | 7/2009 | Gregersen | |

FOREIGN PATENT DOCUMENTS

| | | |
|---|---|---|
| CN | 1795023 A | 6/2006 |
| CN | 101909672 A | 12/2010 |
| JP | 2007521926 A | 8/2007 |
| JP | 2008518707 A | 6/2008 |
| JP | 2011502583 A | 1/2011 |
| WO | 199907301 A1 | 2/1999 |
| WO | 2005077449 A1 | 8/2005 |
| WO | 2006048700 A1 | 5/2006 |
| WO | 2009059220 A1 | 5/2009 |

OTHER PUBLICATIONS

Dr. Sven Ivar Seldinger MD @ Congress of the Northern Assoc. of Medical Radiology at Helsinki in Jun. 1952.
Dr. Shaldon—1961 Edition of The Lancet at pp. 857-859.
Dr. Uldall—Dialysis & Transplantation, vol. 8, No. 10 in Oct. 1979.
Office Action for corresponding Australian Patent Application No. 2013251786 dated Oct. 6, 2016.
Office Action from corresponding Chinese Patent Application No. 201380028826.2 dated Jun. 3, 2016.
Office Action for corresponding Japanese Patent Application No. 2015-509080 dated Nov. 22, 2016.

\* cited by examiner

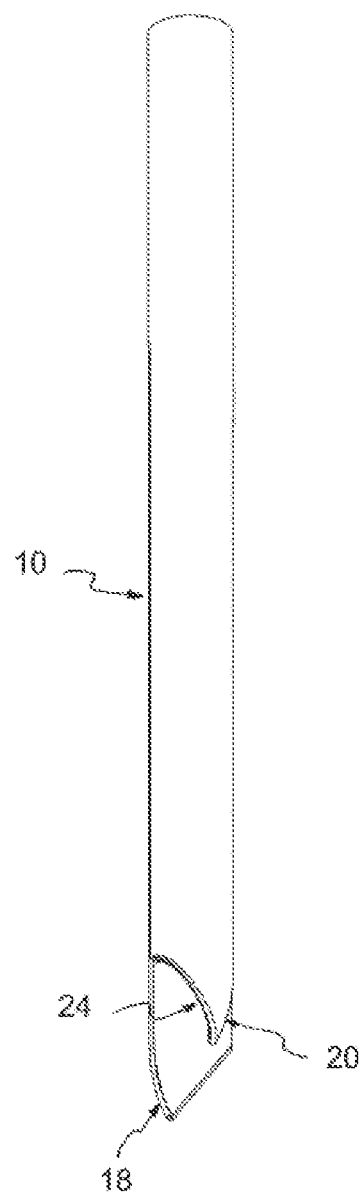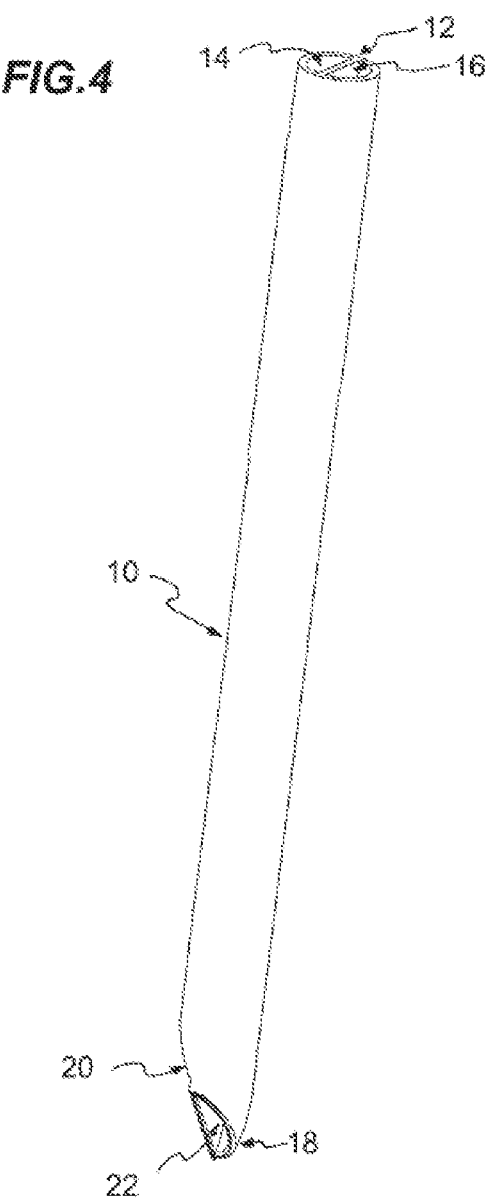

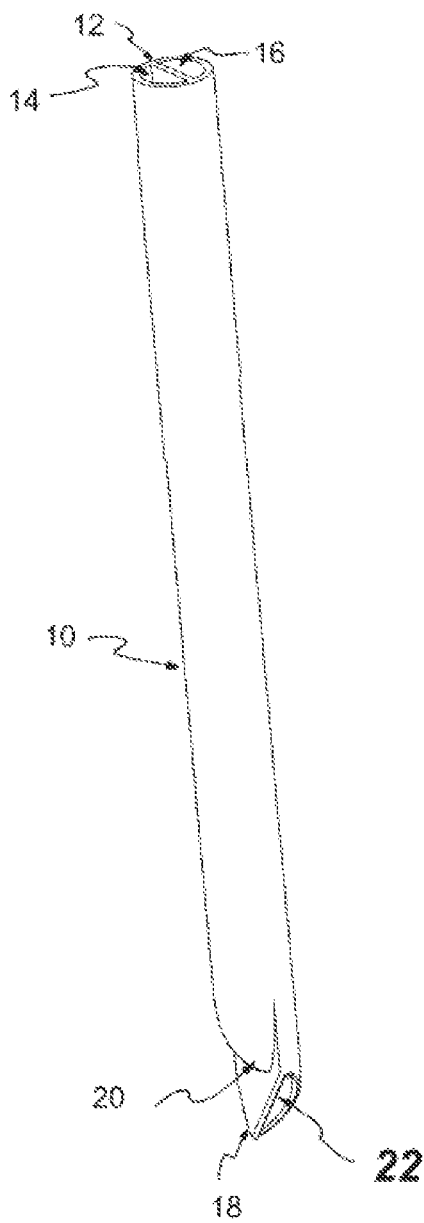

MULTI-LUMEN CATHETER

CROSS REFERENCE TO RELATED APPLICATIONS

This application is a continuation of U.S. patent application Ser. No. 13/453,663, filed Apr. 23, 2012, which claims the priority benefit of U.S. provisional application No. 61/477,815, filed Apr. 21, 2011, and is a continuation-in-part of U.S. patent application Ser. No. 12/479,257, filed Jun. 5, 2009, now U.S. Pat. No. 8,517,978, which is a continuation of U.S. patent application Ser. No. 11/103,778, filed Apr. 12, 2005, now U.S. Pat. No. 7,569,029, which claims the benefit of U.S. provisional application Ser. No. 60/561,430, filed Apr. 12, 2004, each of which is incorporated herein by reference in their entireties.

BACKGROUND

The present invention relates to a multi-lumen catheter and, more specifically, to a dual-lumen catheter with entry and exit ports having curved or angled walls to direct the flow of fluids therethrough.

Dual-lumen catheters have been available for many years for a variety of medical purposes. It is only in recent years, however, that such catheters have been developed for use in hemodialysis and other treatments which involve the removal and replacement of blood. The general form of dual-lumen catheters goes back to as early as 1882 when Pfarre patented such a catheter in the United States under Ser. No. 256,590. This patent teaches a flexible dual-lumen catheter which is used primarily for cleaning and drainage of, for example, the bladder, rectum, stomach and ear. In this type of catheterization, the catheter is introduced into an existing body orifice without the use of any puncturing needle or guide wire.

More recently, a catheter was developed and patented by Blake et al. under U.S. Pat. No. 3,634,924. This patent teaches a double lumen cardiac balloon catheter which is introduced into a large vein and the balloon is inflated to control the flow in the vein. The catheter can be placed by using the balloon as a "sail" to move with the blood from an ante-cubital or other peripheral vein through for example, the right heart chambers into the smaller radicals of the pulmonary artery where the catheter takes up its intended function. This patent teaches the use of two lumina in a single body and explains how to make a tip for a dual-lumen structure of the type which has become common for a variety of purposes including hemodialysis. The structure uses a plug to seal the end of one lumen and a wire which retains the shape of the other lumen during formation of the tip in a heated die.

Further patents which teach dual-lumen or multiple lumen catheters for general use include the following: U.S. Pat. Nos. 701,075; 2,175,726; 2,819,718; 4,072,146; 4,098,275; 4,134,402; 4,180,068; 4,406,656; 4,451,252; 5,221,255; 5,380,276; 5,395,316; 5,403,291; 5,405,341; 6,001,079; 6,190,349; 6,719,749; 6,758,836; and 6,786,884, the disclosures of each of which are incorporated herein in their entirety.

Vascular catheter access techniques have been known to the medical profession for many years and, in fact, can be traced back to the 17th century. However, it was only with the introduction of the Seldinger technique in the early 1950s that a new approach could be used to improve vascular access. This technique was taught in an article published by Dr. Sven Ivar Seldinger resulting from a presentation made at the Congress of the Northern Association of Medical Radiology at Helsinki in June of 1952. The technique essentially involves the use of a hollow needle to make an initial puncture, and a wire is then entered through the needle and positioned in the vessel. The needle is withdrawn and the catheter is entered percutaneously over the wire which is itself later withdrawn. With this technique it became possible to make less traumatic vascular access and this has now become the accepted method of performing access in numerous medical techniques. One of these techniques which been the subject of much research and development is hemodialysis.

Hemodialysis can be defined as the temporary removal of blood from a patient for the purpose of extracting or separating toxins therefrom and the return of the cleansed blood to the same patient. Hemodialysis is indicated in patients where renal impairment or failure exists, that is, in cases where the blood is not being properly or sufficiently cleansed, particularly to remove waste materials and water, by the kidneys.

In the case of chronic renal impairment or failure, hemodialysis has to be carried out on a repetitive basis. For example, in end-stage kidney disease where transplantation of kidneys is not possible or for medical reasons is contra-indicated, the patient may have to be dialyzed about 100 to 150 times per year. This can result in several thousand accesses to the blood stream to enable hemodialysis to be performed over the remaining life of the patient.

Towards the end of 1960, Dr. Stanley Shaldon and colleagues developed, in the Royal Free Hospital in London, England, a technique for hemodialysis by percutaneous catheterization of deep blood vessels, specifically the femoral artery and vein. The technique was described in an article published by Dr. Shaldon and his associates in the Oct. 14, 1961 edition of The Lancet at Pages 857 to 859. Dr. Shaldon and his associates developed single lumen catheters having tapered tips for entry over a Seldinger wire to be used in hemodialysis. Subsequently, Dr. Shaldon and his colleagues began to insert single lumen inlet and outlet catheters in the femoral vein and this was reported in the British Medical Journal of Jun. 19, 1963. The purpose of providing both inlet and outlet catheters in the femoral vein was to explore the possibility of a "self-service" approach to dialysis. Dr. Shaldon was subsequently successful in doing this and patients were able to operate reasonably normally while carrying implanted catheters which could be connected to hemodialysis equipment periodically.

An advantage of dual-lumen catheters in hemodialysis is that only one vein access need be affected to establish continued dialysis of the blood. One lumen serves as the conduit for blood flowing from the patient to the dialysis unit and the other lumen serves as a conduit for treated blood returning from the dialysis unit to the patient. This contrasts with prior systems where either two insertions were necessary to place two separate catheters as was done by Dr. Shaldon, or a single catheter was used with a complicated dialysis machine which alternately removed blood and returned cleansed blood.

The success of Dr. Shaldon in placing catheters which will remain in place for periodic hemodialysis caused further work to be done with different sites. Dr. Shaldon used the femoral vein, and in about 1977 Dr. P. R. Uldall, in Toronto Western Hospital, Canada, began clinical testing of a sub-clavian catheter that would remain in place between dialysis treatments. An article describing this was published by Dr. Uldall and others in Dialysis and Transplantation, Volume 8, No. 10, in October 1979. Subsequently Dr. Uldall began experimenting with a coaxial dual-lumen catheter for subclavian insertion and this resulted in Canadian Patent No. 1,092,927 which issued on Jan. 6, 1981. Although this particular form of catheter has not achieved significant success in the marketplace, it was the forerunner of dual-lumen catheters implanted in the subclavian vein for periodic hemodialysis.

The next significant step in the development of a dual-lumen catheter for hemodialysis is Canadian Patent No. 1,150,122 to Martin. A subsequent development is shown in U.S. Pat. No. 4,451,252 also to Martin. This catheter utilizes the well-known dual-lumen configuration in which the lumina are arranged side-by-side separated by a diametric septum. The structure shown in this patent provides for a tip making it possible to enter a Seldinger wire through one of the lumina and to use this wire as a guide for inserting the catheter percutaneously. This type of structure is shown in a European Patent Application to Edelman published under No. 0 079 719, and in U.S. Pat. Nos. 4,619,643; 4,583,968; 4,568,329; 4,543,087; 4,692,141; 4,568,329, and U.S. Des. Pat. No. 272,651, the disclosures of each of which are incorporated herein in their entirety.

In order to insert a catheter over a guide wire using the Seldinger technique, or indeed any similar technique, the tip of the catheter must possess sufficient rigidity so that it does not concertina as it contacts the skin because this would enlarge the skin puncture as the catheter is being entered over the wire. To some extent this is at odds with the desirable material qualities of the main body of catheter which should be soft and flexible for patient comfort. In an effort to solve this problem, a variety of tips have been formed within the limitations of using a single extrusion from which the body and tip are formed. The result is that the tips have in general been made by using some of the excess material found in the shorter intake lumen. This has led to other problems such as very stiff tips which are unsuitable for prolonged placement in a vein; voids which can accumulate stagnant blood; and short stubby tips which are less desirable for insertion than longer more gradual tips. Also, because there is not always sufficient material to form the tip, plugs have been added with a varying degree of success because if the plug is not placed accurately the resulting structure may have unacceptable spaces where blood can stagnate.

It must also be recognized that the degree of rigidity in the tip becomes more important if the catheter is to reside in the patient for prolonged periods, as is becoming more common in many treatments, notably hemodialysis. This is because although ideally the catheter lies in the middle of the vein, in practice it will often bear against the vessel wall. In such circumstances it is possible that a stiff tip could damage or even embed itself in the vessel wall when left in place for extended periods.

Hemodialysis, as practiced today, normally employs one of two types of catheters to remove blood from the patient for processing and return processed blood to the patient. Most commonly, a dual-lumen catheter is used, each lumen having either a generally cylindrical or semi-cylindrical configuration. Alternatively, two separate tubes, each usually having a full cylindrical configuration, are used separately to remove blood for dialysis and return the processed blood.

Flow rates possible with conventional dual-lumen catheters are usually lower than those achievable where separate tubes are used to remove blood from a vein for dialysis and then return processed blood back to the vein. Thus, the use of two tubes has become more and more popular as the capacity (maximum flow rate) of hemodialysis membranes has increased.

Hemodialysis membranes are now able to process blood at over 500 ml of flow per minute. Even higher processing rates are foreseeable. However, problems occur with both the line introducing purified blood back into the vein and the line removing blood for purification at flow rates above 300 ml per minute. A high flow rate from the venous line may cause whipping or "firehosing" of the tip in the vein with consequent damage to the vein lining A corresponding high flow rate into the arterial line may cause the port to be sucked into the vein wall, resulting in occlusion.

The rate of flow through a catheter lumen, whether it be in a single lumen or a dual-lumen catheter, is controlled by a number of factors including the smoothness of the wall surface, the internal diameter or cross-sectional area of the tube lumen, and the length of the tube lumen. The most important factor is the cross-sectional area of the tube lumen. The force or speed of the fluid flow in a tube lumen for a given cross-sectional area is controlled by the external pumping force. This is a positive pressure pushing processed blood through the venous lumen and a negative (suction) pressure pulling unprocessed blood through the arterial lumen.

Problems encountered in providing for a high flow rate through a catheter are magnified in a dual-lumen catheter construction. Because each of the lumina in a dual-lumen catheter normally has a D-shape, it has been assumed that flow rates are limited. Furthermore, such dual-lumen catheters are, to a great extent, catheters with a main port which opens at the end of a lumen substantially on the axis of the lumen. Thus, firehosing frequently results. Firehosing may damage the vein wall, triggering the build-up of fibrin on the catheter tip. Fibrin build-up may further result in port occlusion.

There are dual lumen-catheters which utilize side ports for both outflow and inflow. An example is the catheter disclosed in U.S. Pat. No. 5,571,093 to Cruz et al. However, such catheters have not been entirely successful in solving problems related to hemodialysis with dual lumen catheters, e.g., high incidences of catheter port occlusion as well as some degree of fire-hosing. Further, the abrupt change in direction of the flow of blood from the vein into the catheter can result in trauma and damage to red blood cells, especially at higher flow rates.

SUMMARY

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this document is to be construed as an admission that the embodiments described in this document are not entitled to antedate such disclosure by virtue of prior invention. As used in this document, the term "comprising" means "including, but not limited to."

An object of the present invention is to provide an improved multi-lumen catheter for use in hemodialysis, plasmapheresis, and other therapies which require removal of blood from one lumen of the catheter and return of treated blood through the other lumen.

Another object is to provide a multi-lumen catheter which is capable of accommodating high flow rates.

Yet another object is to provide a more efficient multi-lumen catheter for use in hemodialysis, plasmapheresis, and other therapies which require removal of blood from one lumen of the catheter and return of treated blood through the other lumen.

Still another object is to provide a multi-lumen catheter which permits high flow rates while reducing trauma to vessel walls and red cell damage.

Yet another object of the present invention is a multi-lumen catheter having a tip configuration which minimizes recirculation by maximizing the control and direction of blood flow into and out from the lumen ports.

The foregoing and other objects are realized in accord with the present invention by providing an apparatus which comprises an elongated catheter body for placement within a vessel, a septum that runs longitudinally through the interior of the catheter body so as to divide the interior of the catheter body into a first lumen and a second lumen each having a distal end having curved or angled internal walls that terminate at ports located on opposing sides of the catheter body. The curved or angled internal walls at the distal end of the lumina provide for a transition zone in which the flow of blood into and out from the catheter travels a path that gradually changes the direction of the flow of fluids between the direction of flow in the lumen and the direction of flow in the vessel.

In one embodiment, the change in direction of the flow pattern into and out of the catheter body is substantially helical. In other embodiments, the direction of the flow pattern into and out of the catheter body is curved, and in still other embodiments the direction of the flow pattern into and out of the catheter body is angled. In this manner, the flow patterns of these embodiments provide for more efficient exchange of blood by creating an alternate pattern of blood dynamics through the catheter lumina and the vessel.

In another embodiment, the ports of the lumina are longitudinally spaced. In this manner the withdrawal of blood to be treated and the return of treated blood are further separated so as to advantageously minimize the recirculation of treated blood with untreated blood. The length of separation may vary according with specific application, and is preferably from about 2 to about 3 centimeters. Preferably, the lumen port associated with the withdrawal of blood from the patient is "upstream" of the lumen port associated with the return of treated blood.

These and other features of the invention will be more fully understood by reference to the following drawings and the detailed description set forth below.

BRIEF DESCRIPTION OF THE DRAWINGS

FIG. 3 illustrates a perspective view of a dual-lumen catheter of the present invention shown apart from inflow and outflow tubing.

FIG. 4 illustrates another perspective view of the dual-lumen catheter of FIG. 3.

FIG. 5 illustrates a third perspective view of the dual-lumen catheter of FIG. 3.

DETAILED DESCRIPTION

Figures 1, 2:
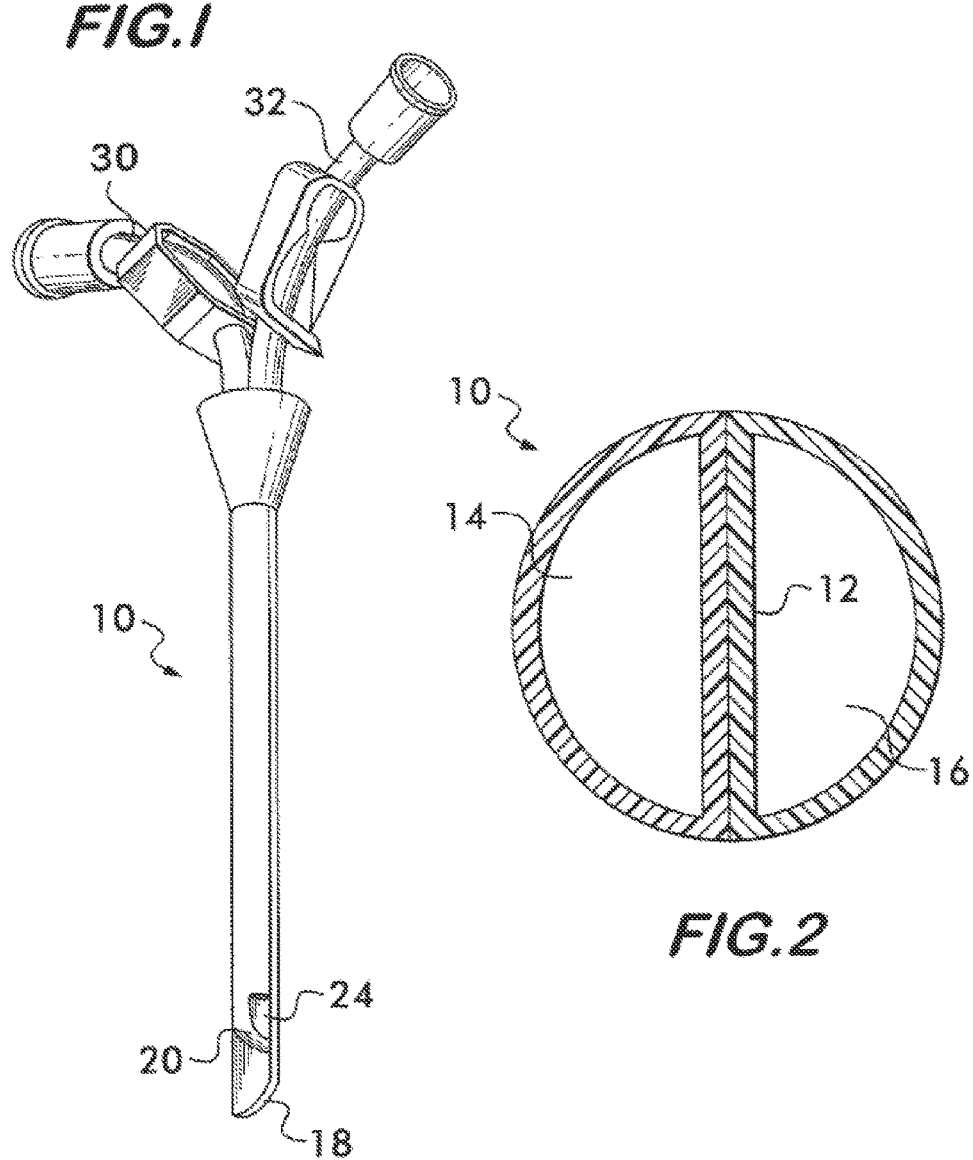
FIG. 1 illustrates a perspective view of a dual-lumen catheter of the present invention attached to inflow and outflow tubing.
FIG. 2 illustrates a cross-sectional view of a dual lumen catheter of FIG. 1
Figure 6A:
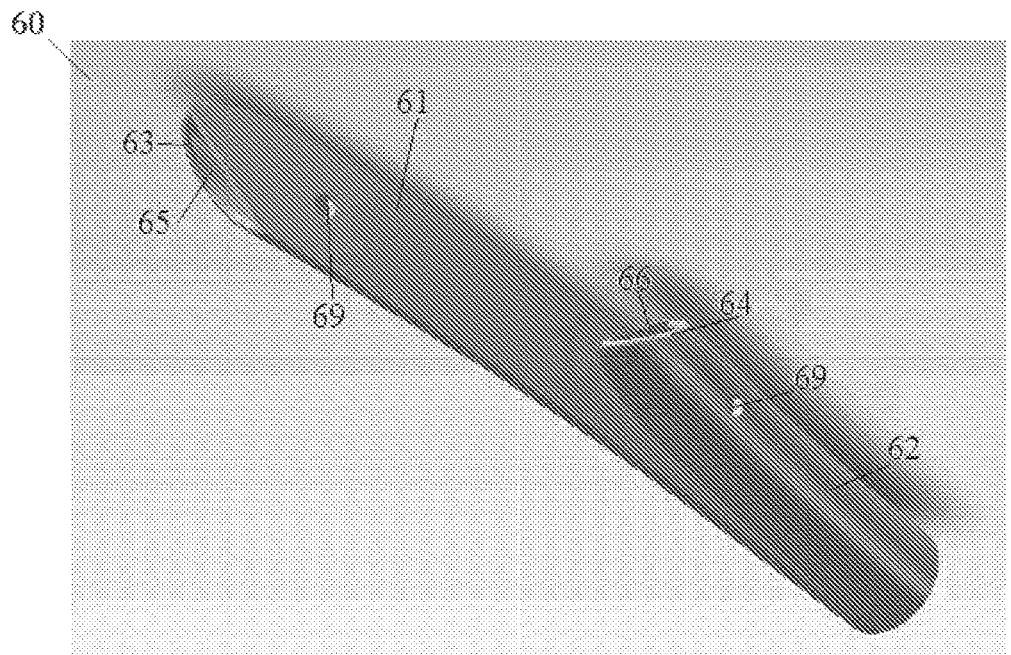
FIGS. 6A-6D illustrate an alternative embodiment of a split tip multi-lumen catheter.
Figure 6B:
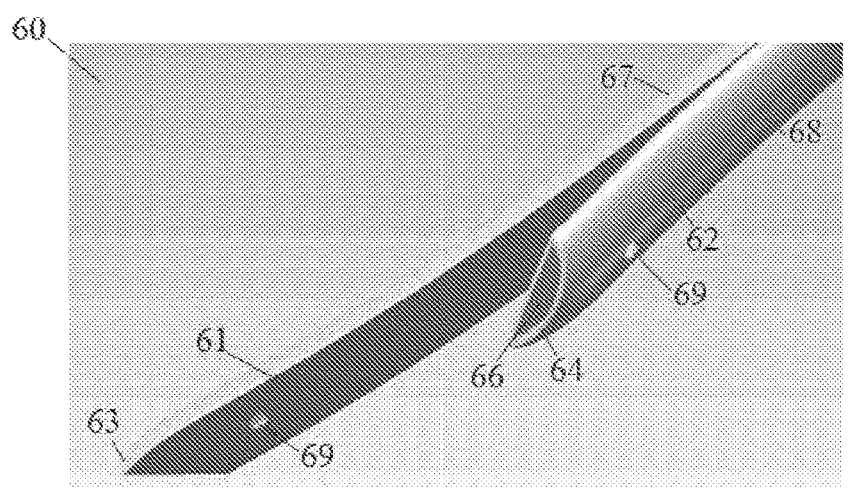
Figure 6C:
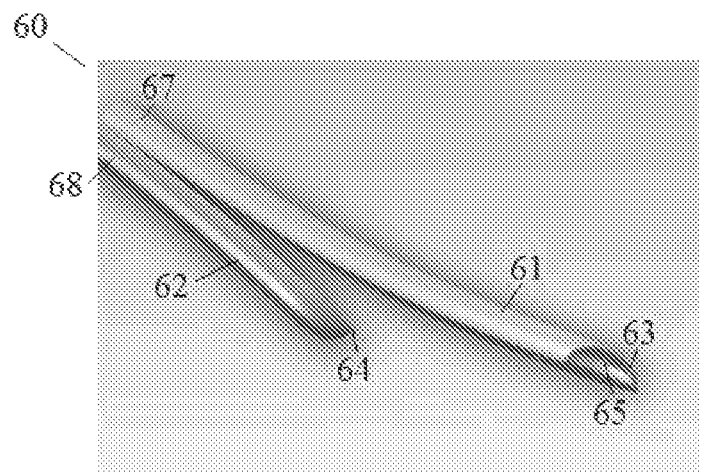
Figure 6D:
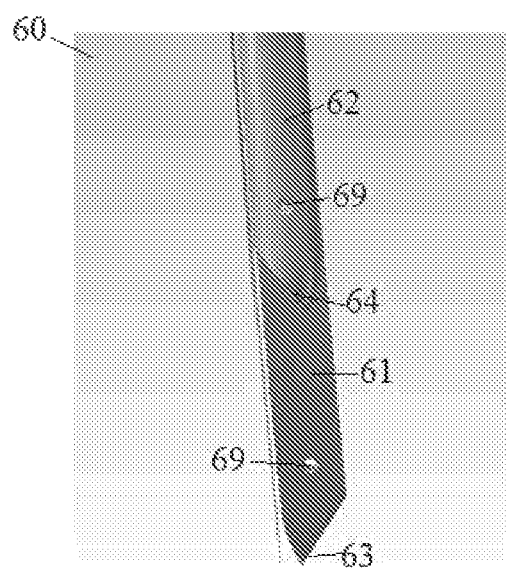
Figure 7A:
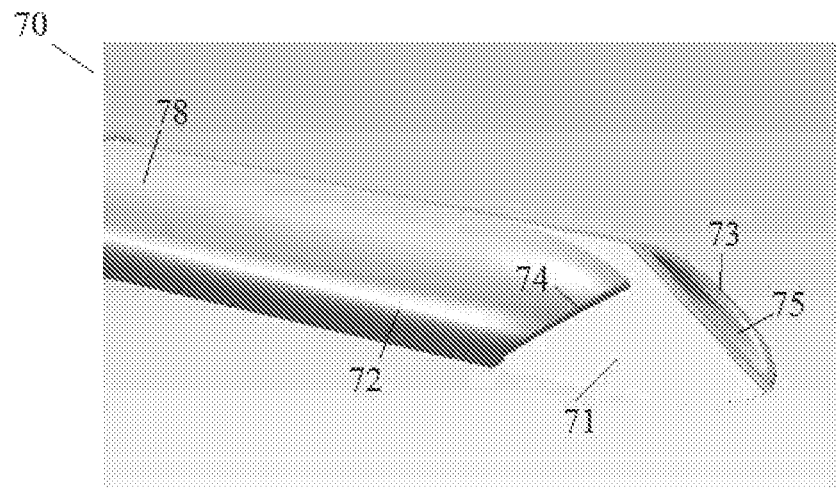
FIGS. 7A-7E illustrate an alternative embodiment of a step tip multi-lumen catheter.
Figure 7B:
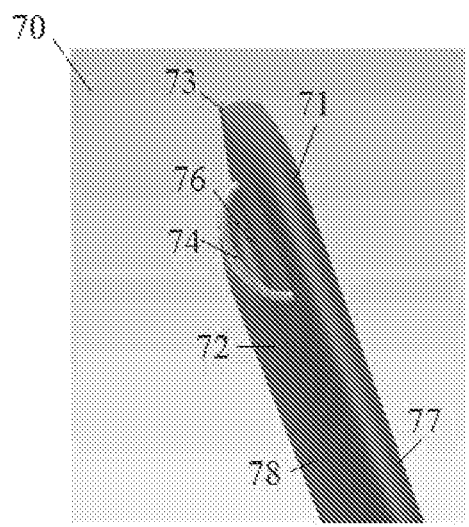
Figure 7C:
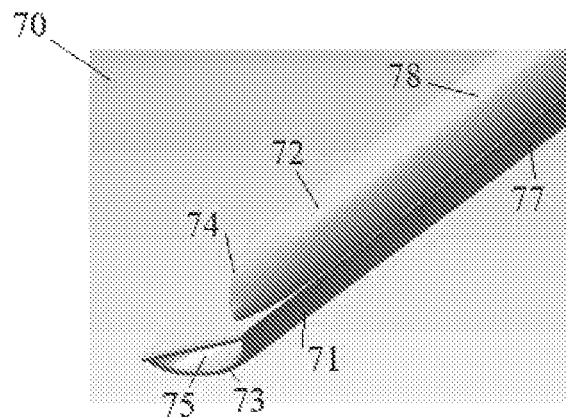
Figure 7D:
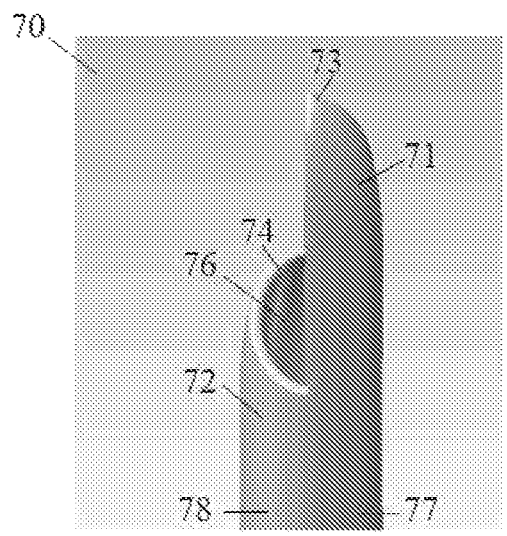
Figure 7E:
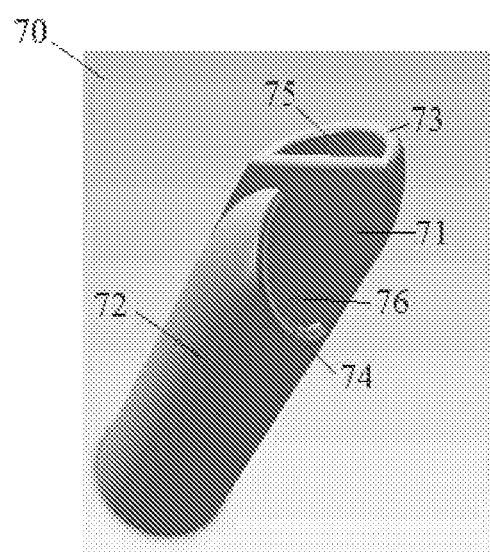

In accordance with the apparatus of the present invention, there is provided a catheter body that is adapted for insertion into a vessel of a patient such as, for example, a vein. The catheter body comprises an external wall and a septum extending longitudinally along the internal length of the catheter body to define two substantially parallel lumina each having an internal wall and a port located at the side of the distal end thereof.

At the distal end of each lumen, at least a portion of the internal walls of the lumina are curved or angled to define a transition zone terminating at the port. So configured, the transition zone permits the flow of fluids traveling the length of the lumen to be gradually deflected from the longitudinal direction of the lumen to the transverse direction of the side-facing port at the distal end thereof.

For fluids entering the side-facing port of the lumen, the transition zone permits the flow to be gradually deflected from the direction of travel through the vessel through the lateral direction of entry to the longitudinal direction of travel in the lumen. In this fashion, the transition zone provides a gradual change in the direction of flow into and out of the lumina. This smoother and more physiologic change of direction of the fluids traveling through the lumina decreases firehosing of the catheter tip during high rates of fluid exchange, reduces stresses experienced by the fluid, and permits a more efficient and higher rate of flow into and out from the catheter. This more gradual change in direction of blood flow also results in less prolongation of blood residence time within the catheter tips which can decrease the likelihood of thrombus formation within the catheter. In the context of hemodialysis, plasmapheresis, and other therapies which require the transport of blood, decrease in stress provided by the transition zones at the distal end of the lumina decreases the incidence of platelet activation, hemolysis and trauma to the vessel lining.

In one embodiment, a first lumen of the catheter terminates in a first bolus cavity, which is formed into one side of a bolus tip at a position between the interfacing section of the lumen and a nose section of the bolus tip. The nose section of the terminal portion of the first lumen may be formed through an injection molding process to create a helical shape of the nose section and first bolus cavity so that fluids such as blood traveling through the lumen have a smooth transition of its direction of flow as it enters the first lumen. The second lumen of the catheter terminates in a second bolus cavity oriented 180° from the first bolus cavity, and possesses a nose section which has a similar injection molded-configuration as the nose tip of the first lumen. The nose sections of the first and second lumina direct blood flow in directions opposite to each other thereby reducing the admixture of treated blood with non-treated blood. Preferably, the second lumen in this embodiment extends beyond the first lumen by about 2 to about 3 centimeters so that the nose section of the terminal portion of the second lumen is longitudinally spaced from the nose section of the terminal portion of the first lumen.

In another embodiment, the terminations of the first and second lumina within the nose section are partly recessed, to enable the overhanging aspect of the nose section to serve as a barrier with the vessel wall. This design is intended to reduce the phenomenon of partial or total occlusion of the lumina of the catheter.

In yet another embodiment, an additional lumen is provided within the catheter body to allow introduction of a guide wire. The guide wire inserted into this additional lumen and used to assist in the introduction and proper placement of the catheter tip into a vessel of a patient. The additional lumen for the guide wire may terminate at the same position as the first and/or second lumina, or may terminate distally beyond the distal ends of the lumina to provide additional stability to the catheter body. In such a configuration, the substantially helical transition zones of the first and second lumina may be created through mechanically or thermally (e.g., with a laser) skiving the apertures within the terminal shafts of the catheter.

In still another embodiment, the first and second lumina may be split apart along the distal portion of the septum by, for example, a splittable membrane in the septum. In this manner, the lumina may be partially longitudinally separated from each other.

As used herein, reference to curvature or angularity with regard to the internal walls of the lumina includes a wide range of configurations in which at least a portion of the internal walls of the lumen at the distal ends thereof undergoes a transition in direction from the longitudinal direction of the lumen to a direction angled from such longitudinal direction. In this fashion, fluids traveling in either direction through the lumen will bear against the curved or angled wall in the transition zone in changing direction from or to a longitudinal orientation.

This change in the direction of the internal wall of the lumen in the transition zone may be constant or may vary along some or all of the transition zone, and may extend along two dimensions in which the flow path changes direction substantially within a single plane, or through three dimensions. Preferably, the curvature or angularity of the internal walls of the lumina extends in three dimensions and is substantially helical. As used herein, helical patterns includes patterns that are regular and irregular and with constant or varying diameters along their length. So configured, the movement of fluids through the transition zone imparts a helical flow pattern to such fluids. This helical flow pattern reduces the incidence of in-plane recirculation. In the context of hemodialysis, plasmapheresis, and other therapies which require the transport of blood, this helical flow pattern reduces the incidence of treated blood that is delivered to the patient through the catheter to re-enter the catheter at the intake port. The reduction of this type of recirculation allows for more efficient blood exchange and, consequently, reduced treatment time.

The cross-sectional area and geometry of the lumina may be similar to or different from each other. Preferably, the cross-sectional area of each lumen is similarly sized in order to accommodate similar flow volumes and rates into and out from the catheter. In preferred from, the cross-sectional area of each lumen is from about 3.5 mm to about 5 ram, and more preferably from about 4.5 mm to about 5 mm. The cross-section geometry of the lumina may assume a variety of shapes including circular, semi-circular (D-shaped), elliptical, semi-elliptical, teardrop-shaped, or curved teardrop-shaped resembling a yin-yang symbol.

The ports provided in the side walls of the distal ends of the lumina may accommodate a range of sizes and shapes including circular, semi-circular (D-shaped), elliptical, semi-elliptical, teardrop-shaped. Preferably, the ports are semi-elliptical and are from about 3 to about 6 mm in maximal diameter. The terminating cavities of the first and second channels have a greater surface area than prior designs, such us that shown in U.S. Pat. No. 4,808,155 by Mahurkar. This results in more efficient exchange of fluids and blood.

The catheter of the present invention may be constructed from materials that are commonly used for multi-lumen catheters such as silicone or polyurethanes including polyurethanes sold under the trademark Carbothane® by Carboline Company of St. Louis, Mo.

In another aspect of the present invention, there is provided a method for exchanging fluids in a patient comprising the step of positioning a catheter of the present invention in communication with a fluid-containing vessel of a patient. In preferred embodiments, the exchanged fluid comprises blood and the fluid-containing vessel of the patient is a vein. The method of the present invention is particularly well-suited to the performance of hemodialysis, plasmapheresis, and other therapies which require removal and return of blood from a patient. The method of the present invention may further comprise the steps of ultrafiltration and/or venous sampling.

Turning now to the embodiment that is shown in the drawings and referring to FIGS. 1-5, there is shown a catheter 10 having a septum 12 bisecting the interior of catheter 10 to form two lumina 14 and 16. At the distal end of catheter 10, the lumina 14 and 16 have with curved walls 18 and 20 which terminate at ports 22 and 24 disposed on opposite sides of catheter 10. As shown in FIG. 2, the cross-section shape of lumina 14 and 16 are semicircular. In the catheter shown in FIGS. 1 and 3-5, lumen 16 extends beyond the end of lumen 14 so as to further separate the intake port 24 from outflow port 22. In operation, fluid, such as blood, enters intake port 24, changes direction as the flow of fluid passes curved wall 20 through lumen 14 to tube 32 which conveys the fluid for treatment to a device such as a dialysis machine (not shown). After treatment, the treated fluid is returned to a patient through tube 30 to lumen 16. At the end of lumen 16, the fluid is deflected by curved wall 18 and out port 22 into the vessel of the patient.

FIGS. 6A-6D illustrate an alternative embodiment of a multi-lumen catheter. The catheter 60 includes a split tip to form two lumina 61 and 62. The split design eliminates the shared septum used to bisect the interior of the catheter. Each lumen 61 and 62 has a unique wall that defines their shape. At the distal end of the catheter 60, the lumina 61 and 62 may have with curved walls 63 and 64 which terminate at ports 65 and 66 disposed on opposite sides of catheter 60. As shown by way of example only, the lumen 61 extends beyond the end of lumen 62 so as to further separate the intake port 65 from outflow port 66. In operation, fluid, such as blood, enters intake port 65, changes direction as the flow of fluid passes curved wall 63 through lumen 61 to tube 67 which conveys the fluid for treatment to a device such as a dialysis machine (not shown). After treatment, the treated fluid is returned to a patient through tube 68 to lumen 62. At the end of lumen 62, the fluid is deflected by curved wall 64 and out port 66 into the vessel of the patient.

In operation, the lumina 61 and 62 of the catheter 60 may be attached with a weak adhesive to maintain structural integrity of the catheter during operation. The adhesive may be water-soluble such that blood flow around the catheter 60 causes the adhesive to dissolve, thereby causing at least a portion of the lumina 61 and 62 to split. For example, the catheter 60 may be manufactured such that the last 5 cm of the catheter have the water-soluble adhesive and thus split when the adhesive dissolves.

Based upon the intended fluid flow and acceptable disruption of the fluid, one or more side holes 69 may be included in the catheter 60. The side holes 69 may assist in providing additional means of blood or other fluid exchange as well as serve as a mounting point for attaching the catheter 60 on a guide wire during insertion/removal/exchange from a patient.

The side holes 69 may be sized and positioned such that fluid flow is optimized about the lumen tips. For example, the side holes 69 may be approximately 1 mm in diameter, and be positioned approximately 1 cm from the ports 65 and 66. Alternatively, the side holes may be smaller (e.g., 0.5 mm), larger (e.g., 1.5 mm), or positioned in another location (e.g., 1.5 cm from the ports). The size and location of the side holes 69 may produce changes in shear stress and blood cell residence time at the catheter tips, and thus the optimal balance may incorporate side holes being approximately 0.75 mm to 1.2 mm in diameter.

Using properly spaced and sized side holes, such as side holes 69, may result in a highly optimized catheter. For example, by using a similar catheter to the catheter 60 as shown in FIGS. 6A-6D, fluid flow through the catheter may be optimized while recirculation is greatly reduced.

It should be noted that side holes 69 as shown in FIGS. 6A-6D are shown by way of example only. Additional or alternative apertures such as slits, flaps, semicircular cuts, and other similar shapes may be used. Additionally, the side holes may have a helical contour to produce additional deflection to any fluid flowing therethrough.

As shown in FIGS. 6A-6D, the curved walls 63 and 64 define an area of deflection such that fluid flowing through the catheter 60 is deflected. Depending on the application of the catheter 60, and the amount of desired deflection, an angle of the curved walls 63 and 64 may vary accordingly. For example, the curved walls 63 and 64 may be approximately 54°. Alternatively, the curved walls 63 and 64 may be between the range of 0° and 90°. Typically, 0° and 90° may not be used as they both have inherent drawbacks. 0° would cause no deflection to the fluid, 90° would result in the port being perpendicular to the axial flow path of the catheter. On the input port, this could cause a vacuum force which attaches the associated lumina to the side of a blood vessel. While a side hole would help to alleviate any potential vacuum pressure, overall performance of the catheter would still decrease.

FIGS. 7A-7E illustrate an alternative embodiment of a multi-lumen catheter. The catheter 70 includes a stepped tip to form two lumina 71 and 72. Like the split design, this design results in one lumen being longer than the other. The stepped tip design also eliminates a septum at the tip to bisect the interior of the catheter to form two ports where the septum extends beyond the ports. Rather, each lumina 71 and 72 has a unique curved wall that defines their shape and the flow of fluid therethrough such that no extended septum is required to maintain fluid separation.

At the distal end of the catheter 70, the lumina 71 and 72 may have with curved walls 73 and 74 which terminate at ports 75 and 76 disposed on opposite sides of catheter 70. As shown by way of example only, the lumen 71 extends beyond the end of lumen 72, thereby forming a stepped tip design and further separating the intake port 75 from outflow port 76. As before, in operation, fluid, such as blood, enters intake port 75, changes direction as the flow of fluid passes curved wall 73 through lumen 71 to tube 77 which conveys the fluid for treatment to a device such as a dialysis machine (not shown). After treatment, the treated fluid is returned to a patient through tube 78 to lumen 72. At the end of lumen 72, the fluid is deflected by curved wall 74 and out port 76 into the vessel of the patient.

Similar to the discussion above in reference to FIGS. 6A-6D, one or more side holes (not shown in FIGS. 7A-7E) may be included in the catheter 70. The side holes 79 may assist in providing additional means of blood or other fluid exchange as well as serve as a mounting point for attaching the catheter 70 on a guide wire during catheter insertion and/or removal and/or exchange from a patient.

As shown in FIGS. 7A-7E, the curved walls 73 and 74 define an area of deflection such that fluid flowing through the catheter 70 is deflected. Depending on the application of the catheter 70, and the amount of desired deflection, an angle of the curved walls 73 and 74 may vary accordingly. For example, the curved walls 73 and 74 may be approximately 54°. Alternatively, the curved walls 73 and 74 may be between the range of 0° and 90°. Typically, 0° and 90° may not be used as they both have inherent drawbacks. 0° would cause no deflection to the fluid. 90° would result in the port being perpendicular to the axial flow path of the catheter. On the input port, this could cause a vacuum force which attaches the associated lumina to the side of a blood vessel. While a side hole would help to alleviate any potential vacuum pressure, overall performance of the catheter would still decrease.

Figure 8A:
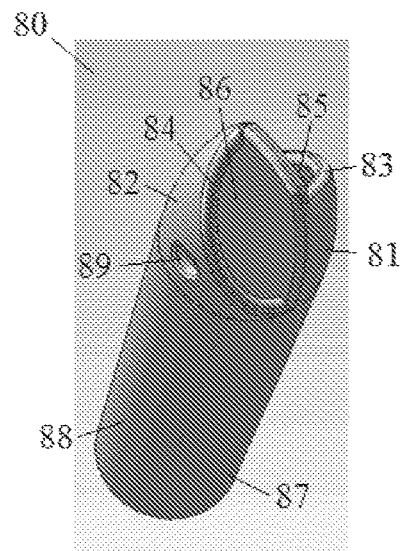
FIGS. 8A-8E illustrate an alternative embodiment of a symmetrical tip multi-lumen catheter.
Figure 8B:
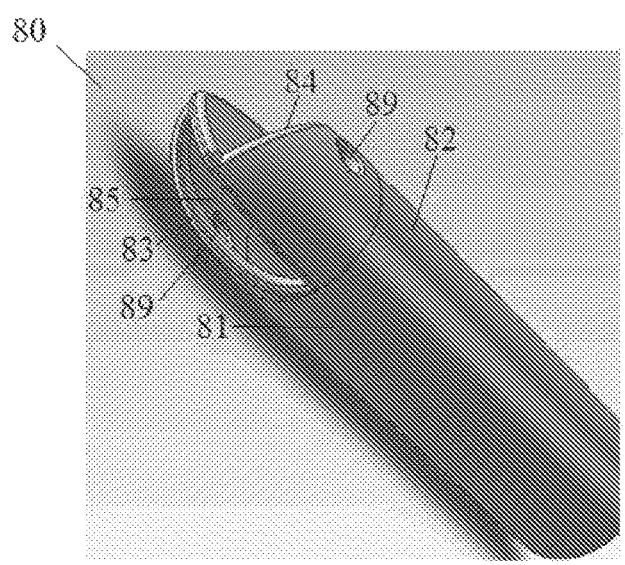
Figure 8C:
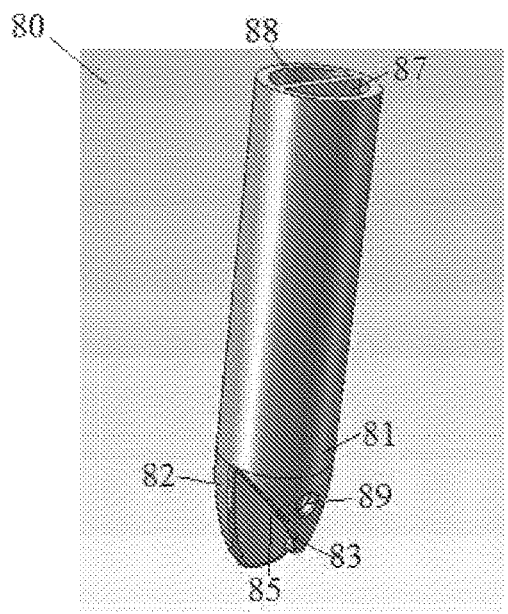
Figure 8D:
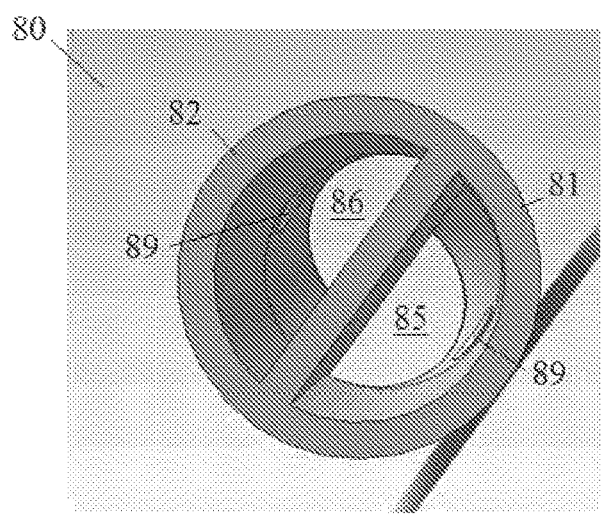
Figure 8E:
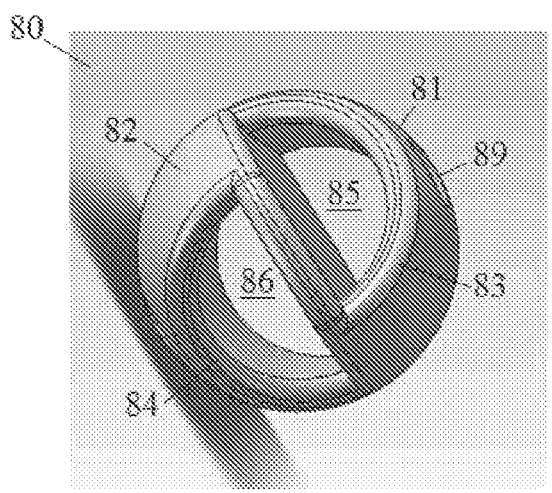

FIGS. 8A-8E illustrate an alternative embodiment of a multi-lumen catheter. The catheter 80 includes a symmetrical tip where two lumina 81 and 82 terminate at the same point such that the ports are adjacent. Additionally, unlike common prior art, the symmetrical tip design as shown herein also eliminates the septum extending beyond the distal ends of the lumina 81 and 82 such that the septum extends beyond the ports. Rather, the septum is trimmed such that it terminates concurrent to the ports. Each lumen 81 and 82 has a unique curved wall that defines their shape and the flow of fluid therethrough such that no extended septum is required to maintain fluid separation. As shown in FIG. 8D, the cross-section shape of lumina 81 and 82 are semicircular.

At the distal end of the catheter 80, the lumina 81 and 82 may have with curved walls 83 and 84 which terminate at ports 85 and 86 disposed on opposite sides of catheter 80. In this symmetrical tip embodiment, the lumen 81 extends to same point as the lumen 82, thereby forming a symmetrical tip design. As before, in operation, fluid, such as blood, enters intake port 85, changes direction as the flow of fluid passes curved wall 83 through lumen 81 to tube 87 which conveys the fluid for treatment to a device such as a dialysis machine (not shown). After treatment, the treated fluid is returned to a patient through tube 88 to lumen 82. At the end of lumen 82, the fluid is deflected by curved wall 84 and out port 86 into the vessel of the patient. By providing the curved walls 83 and 84 to deflect the fluid, the design eliminates the septum extending beyond the ports while still maintaining a low level of fluid from the out port 86 mixing with fluid entering the intake port 85.

Similar to the discussion above in reference to FIGS. 6A-6D, one or more side holes 89 may be included in the catheter 80. The side holes 89 may assist in providing additional means of blood or other fluid exchange as well as serve as a mounting point for attaching the catheter 80 on a guide wire during insertion and/or removal and/or exchange from a patient.

The side holes 89 may be sized and positioned such that fluid flow is optimized about the lumen tips. For example, the side holes 89 may be approximately 1 mm in diameter, and be positioned approximately 1 cm from the ports 85 and 86. Alternatively, the side holes may be smaller (e.g., 0.5 mm), larger (e.g., 1.5 mm), or positioned in another location (e.g., 1.5 cm from the ports). The size and location of the side holes 89 may produce changes in shear stress and blood cell residence time at the catheter tips, and thus the optimal balance may incorporate side holes being approximately 0.75 mm to 1.2 mm in diameter.

Using properly spaced and sized side holes, such as side holes 89, may result in a highly optimized catheter. For example, by using a similar catheter to the catheter 80 as shown in FIGS. 8A-8E, fluid flow through the catheter may be optimized while recirculation is greatly reduced.

It should be noted that side holes 89 as shown in FIGS. 8A-8E are shown by way of example only. Additional or alternative apertures such as slits, flaps, semicircular cuts, and other similar shapes may be used. Additionally, the side holes themselves may have a helical contour to produce additional deflection to any fluid flowing therethrough.

As shown in FIGS. 8A-8E, the curved walls 83 and 84 define an area of deflection such that fluid flowing through the catheter 80 is deflected. Depending on the application of the catheter 80, and the amount of desired deflection, an angle of the curved walls 83 and 84 may vary accordingly. For example, the curved walls 83 and 84 may be approximately 54°. Alternatively, the curved walls 83 and 84 may be between the range of 0° and 90°. Typically, 0° and 90° may not be used as they both have inherent drawbacks. 0° would cause no deflection to the fluid. 90° would result in the port being perpendicular to the axial flow path of the catheter. On the input port, this could cause a vacuum force which attaches the associated lumina to the side of a blood vessel. While a side hole would help to alleviate any potential vacuum pressure, overall performance of the catheter would still decrease.

Figure 9A:
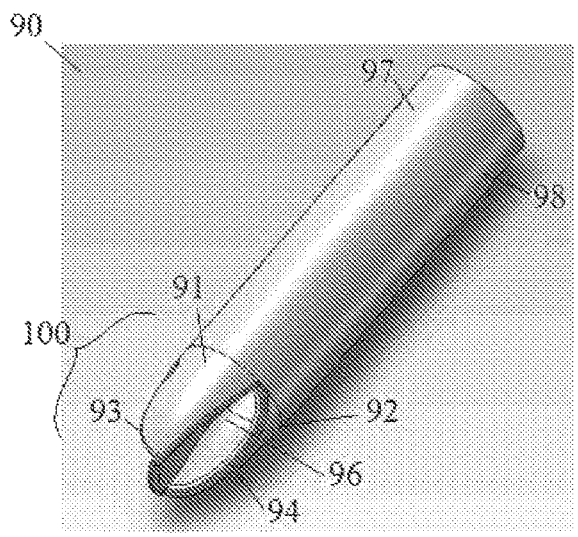
FIGS. 9A-9D illustrate an alternative embodiment of a symmetrical tip multi-lumen catheter having a spiral twisting septum.
Figure 9B:
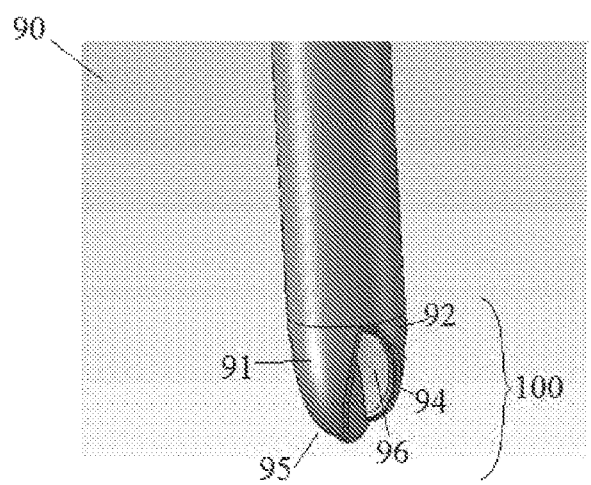
Figure 9C:
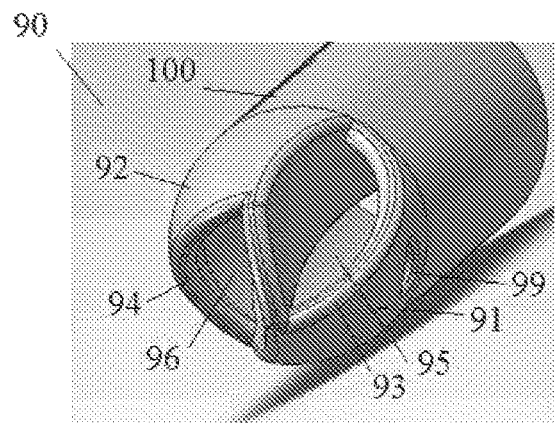
Figure 9D:
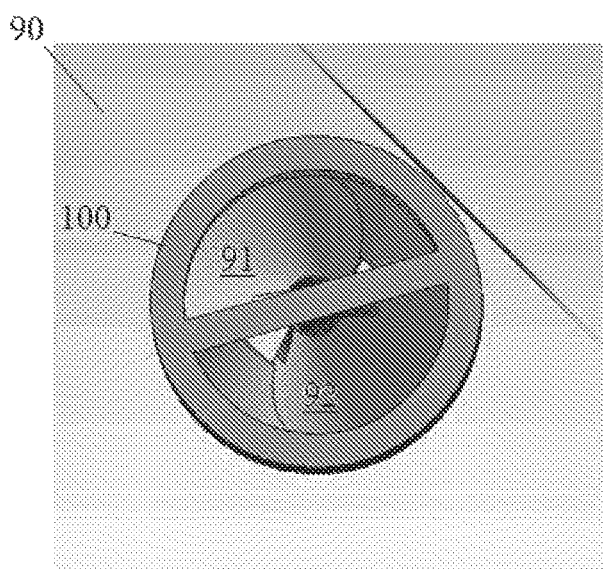

FIGS. 9A-9D illustrate an alternative embodiment of a multi-lumen catheter. The catheter 90 includes a symmetrical tip where two lumina 91 and 92 terminate at the same point such that the ports are adjacent. Additionally, unlike common prior art, the symmetrical tip design as shown herein also eliminates the septum extending beyond the distal ends of the lumina 91 and 92 such that the septum extends beyond the ports. Rather, the septum is trimmed such that it terminates concurrent to the ports. Each lumen 91 and 92 has a unique curved wall that defines their shape and the flow of fluid therethrough such that no extended septum is required to maintain fluid separation. As shown in FIG. 9D, the cross-section shape of lumina 91 and 92 are semicircular.

Unlike the catheter 80 as shown in FIGS. 8A-8E, the catheter 90 includes a spiral twist at the distal end. As shown in FIG. 9C, the twisted portion 100 of the catheter 90 with the spiral twist may be rotated between 1° and 359°, however, an optimum value would be somewhere in the middle of this range, depending on the viscosity and volume of fluid being moved through the catheter. For example, for a catheter to be used for human dialysis, a rotation of about 135° within about 4 cm extending from the distal end of the catheter may be optimal. Alternatively, a range of about 120° to about 150° within an approximate 1 cm to 5 cm extending from the distal end of the catheter may be optimal.

At the distal end of the catheter 90, the lumina 91 and 92 may have with curved walls 93 and 94 which terminate at ports 95 and 96 disposed on opposite sides of catheter 90. In this symmetrical tip embodiment, the lumen 91 extends to same point as the lumen 92, thereby forming a symmetrical tip design. As before, in operation, fluid, such as blood, enters intake port 95, changes direction as the flow of fluid passes curved wall 93 and through the twisted portion 100 of lumen 91 to tube 97 which conveys the fluid for treatment to a device such as a dialysis machine (not shown). After treatment, the treated fluid is returned to a patient through tube 98 to lumen 92. At the end of lumen 92, the fluid is deflected by the twisted portion 100 and the curved wall 94, and passes through out port 96 into the vessel of the patient. By providing the curved walls 93 and 94 and the twisted portion 100 to deflect the fluid, this design eliminates the septum extending beyond the ports while still maintaining a low level of fluid from the out port 96 mixing with fluid entering the intake port 95.

Similar to the discussion above in reference to FIGS. 6A-6D, one or more side holes 99 may be included in the catheter 90. The side holes 99 may assist in providing additional means of blood or other fluid exchange as well as serve as a mounting point for attaching the catheter 90 on a guide wire during insertion and/or removal and/or exchange from a patient.

The side holes 99 may be sized and positioned such that fluid flow is increased about the lumen tips. For example, the side holes 99 may be approximately 1 mm in diameter, and be positioned approximately 1 cm from the ports 95 and 96. Alternatively, the side holes may be smaller (e.g., 0.5 mm), larger (e.g., 1.5 mm), or positioned in another location (e.g., 1.5 cm from the ports). The size and location of the side holes 99 may produce changes in shear stress and blood cell residence time at the catheter tips, and thus the optimal balance may incorporate side holes being approximately 0.75 mm to 1.2 mm in diameter.

Using properly spaced and sized side holes, such as side holes 99, may result in a highly optimized catheter. For example, by using a similar catheter to the catheter 90 as shown in FIGS. 9A-9D, fluid flow through the catheter may be optimized while recirculation is greatly reduced.

It should be noted that side holes 99 as shown in FIGS. 8A-8E are shown by way of example only. Additional or alternative apertures such as slits, flaps, semicircular cuts, and other similar shapes may be used. Additionally, the side holes themselves may have a helical contour to produce additional deflection to any fluid flowing therethrough.

As shown in FIGS. 9A-9D, the curved walls 93 and 94 define an area of deflection such that fluid flowing through the catheter 90 is deflected. Depending on the application of the catheter 90, and the amount of desired deflection, an angle of the curved walls 93 and 94 may vary accordingly. For example, the curved walls 93 and 94 may be approximately 54°. Alternatively, the curved walls 93 and 94 may be between the range of 0° and 90°. Typically, 0° and 90° may not be used as they both have inherent drawbacks. 0° would cause no deflection to the fluid. 90° would result in the port being perpendicular to the axial flow path of the catheter. On the input port, this could cause a vacuum force which attaches the associated lumina to the side of a blood vessel. While a side hole would help to alleviate any potential vacuum pressure, overall performance of the catheter would still decrease.

Although the invention has been described in language specific to structural features and/or methodological acts, it is to be understood that the invention defined in the appended claims is not necessarily limited to the specific features or acts described. Rather, the specific features and acts are disclosed as exemplary forms of implementing the claimed invention.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

I claim:

1. A catheter for placement within a vessel of a patient comprising:
    an elongated catheter body having a proximal end and a distal end; and a septum extending longitudinally through at least a portion of the interior of the catheter body, thereby dividing the interior of the catheter body into a first lumen and a second lumen; wherein each of the first lumen and the second lumen comprise curved internal walls at the distal end of the catheter that terminate at ports located on opposing sides of the catheter body such that fluid flowing through the ports is deflected within a single plane.

2. The catheter of claim 1, wherein a distal end of the first lumen extends beyond a distal end of the second lumen.

3. The catheter of claim 2, wherein the distal end of the first lumen extends from about 2 cm to about 3 cm beyond the distal end of the second lumen.

4. The catheter of claim 1, wherein the first lumen and the second lumen are split apart.

5. The catheter of claim 1, wherein the first lumen and the second lumen are the same length such that the ports are adjacent to one another.

6. The catheter of claim 1, wherein at least one of the first lumen and the second lumen comprises at least one aperture.

7. The catheter of claim 6, wherein the at least one aperture is a side hole.

8. The catheter of claim 1, wherein at least a portion of the catheter is spirally twisted, thereby further deflecting fluid flowing through the catheter.

9. A catheter for placement within a vessel of a patient comprising:
    an elongated catheter body having a proximal end and a distal end; a first lumen comprising a first internal wall at the distal end of the catheter that forms an input port, wherein the first internal wall is curved such that fluid flowing through the input port is deflected within a single plane; a second lumen comprising a second internal wall at the distal end of the catheter that forms an out port, wherein the second internal wall is curved such that fluid flowing through the out port is deflected within a single plane; and a septum extending longitudinally through at least a portion of the interior of the catheter body, thereby dividing the interior of the catheter body into the first lumen and the second lumen.

10. The catheter of claim 9, wherein a distal end of the first lumen extends beyond a distal end of the second lumen.

11. The catheter of claim 10, wherein the distal end of the first lumen extends from about 2 cm to about 3 cm beyond the distal end of the second lumen.

12. The catheter of claim 9, wherein the first lumen and the second lumen are split apart.

13. The catheter of claim 9, wherein the first lumen and the second lumen are the same length such the input port and the out port are adjacent to one another.

14. The catheter of claim 9, wherein at least one of the first lumen and the second lumen comprises at least one aperture.

15. The catheter of claim 14, wherein the at least one aperture is a side hole.

16. The catheter of claim 9, wherein at least a portion of the catheter is spirally twisted, thereby further deflecting fluid flowing through the catheter.

* * * * *